United States Patent
Waksal

(10) Patent No.: US 10,874,624 B2
(45) Date of Patent: Dec. 29, 2020

(54) STABLE TRIENTINE FORMULATIONS

(71) Applicant: KADMON PHARMACEUTICALS, LLC, New York, NY (US)

(72) Inventor: Samuel D. Waksal, New York, NY (US)

(73) Assignee: KADMON PHARMACEUTICALS, LLC, New York, NY (US)

(*) Notice: Subject to any disclaimer, the term of this patent is extended or adjusted under 35 U.S.C. 154(b) by 0 days.

(21) Appl. No.: 15/548,345

(22) PCT Filed: Feb. 3, 2016

(86) PCT No.: PCT/US2016/016430
§ 371 (c)(1),
(2) Date: Aug. 2, 2017

(87) PCT Pub. No.: WO2016/126860
PCT Pub. Date: Aug. 11, 2016

(65) Prior Publication Data
US 2018/0015053 A1   Jan. 18, 2018

Related U.S. Application Data

(60) Provisional application No. 62/111,522, filed on Feb. 3, 2015.

(51) Int. Cl.
*A61K 31/132* (2006.01)
*A61K 45/06* (2006.01)
*A61K 31/13* (2006.01)

(52) U.S. Cl.
CPC ............ *A61K 31/132* (2013.01); *A61K 31/13* (2013.01); *A61K 45/06* (2013.01)

(58) Field of Classification Search
CPC ....... A61K 31/13; A61K 31/132; A61K 45/06
See application file for complete search history.

(56) References Cited

U.S. PATENT DOCUMENTS

| | | | |
|---|---|---|---|
| 2004/0077708 A1* | 4/2004 | Grahek | A61K 9/2013 514/423 |
| 2006/0100278 A1 | 5/2006 | Cooper et al. | |
| 2009/0030079 A1 | 1/2009 | Levinson et al. | |
| 2013/0345311 A1 | 12/2013 | Jonas et al. | |
| 2014/0262883 A1 | 9/2014 | Devouassoux et al. | |

FOREIGN PATENT DOCUMENTS

| | | |
|---|---|---|
| JP | 06135825 A | 5/1994 |
| JP | 2007-246092 A | 9/2007 |
| JP | 2008-525527 A | 7/2008 |
| WO | 2004/009072 A2 | 1/2004 |
| WO | 2006/071844 A2 | 7/2006 |
| WO | 2012/003189 A1 | 1/2012 |

OTHER PUBLICATIONS

Pilchik, R. "Pharmaceutical Blister Packaging, Part 1"; Pharmaceutical Technology (2000); pp. 68-77.
Merck & Co., Inc., Capsules Syprine (R); 1999; 4 pgs.

* cited by examiner

*Primary Examiner* — Savitha M Rao
(74) *Attorney, Agent, or Firm* — Fox Rothschild LLP

(57) ABSTRACT

Provided are pharmaceutical dosage forms comprising (i) trientine or a pharmaceutically acceptable salt of trientine, in a (ii) sealed packaging. The sealed packaging provides a high barrier protection against air, moisture and light and prevents exposure of the drug to conditions that facilitate its decomposition. The pharmaceutical dosage forms are useful for treating diseases or conditions where excess copper is not removed from the body, e.g., Wilson's disease.

19 Claims, No Drawings

STABLE TRIENTINE FORMULATIONS

CROSS-REFERENCE TO RELATED APPLICATIONS

This application claims priority from U.S. Provisional Patent Application Ser. No. 62/111,522, filed Feb. 3, 2015, the disclosures of which are incorporated herein by reference in their entirety.

FIELD OF THE INVENTION

The present invention is directed pharmaceutical dosage forms containing one or more therapeutic amine or polyamine copper chelators, for example, trientine and trientine salts, for the treatment of diseases. The present invention also relates to compositions and methods of stabilizing the polyamine copper chelator. The present invention provides a stable pharmaceutical formulation of trientine or a salt thereof, which does not exhibit substantial decomposition of the active ingredient during the time between final manufacture of the formulation and the use by the patient.

BACKGROUND

Trientine is an organic polyamine compound with the formula $[CH_2NHCH_2CH_2NH_2]_2$. The chemical structure is:

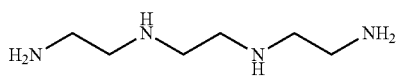

Trientine is also known as N,N'-Bis(2-aminoethyl)ethane-1,2-diamine, triethylenetetramine and trien. Trientine hydrochloride, under the name SYPRINE®, is available as 250 mg capsules for oral administration for the treatment of Wilson's disease.

Wilson's Disease, or hepatolenticular degeneration, is a genetic disorder that effects the metabolism of copper in the body. In Wilson's disease, excess copper is not removed from the body and can accumulate to toxic levels in the liver, brain and other tissues. Wilson's disease is fatal unless detected and treated before serious illness from copper toxicity develops. Trientine is a chelating agent and is used to bind the excess copper by forming a stable complex with the copper, which is then removed from the body by urinary excretion.

The present formulations of trientine have the disadvantage that they must be stored under refrigeration (2-8° C.) to prevent degradation. There exists a need in the art for stable trientine formulations in which the degradation of the trientine is substantially prevented, particularly at ambient (i.e. room) temperatures.

SUMMARY OF THE INVENTION

It is an object of the present invention to provide a pharmaceutical dosage form and a method for the stabilization of trientine.

The pharmaceutical dosage form of the present invention comprises (i) trientine or a pharmaceutically acceptable salt of trientine, in a (ii) sealed packaging. The sealed packaging provides a high barrier protection against air, moisture and light and prevents exposure of the drug to conditions that can facilitate its decomposition. In preferred embodiments, the trientine is packaged under an inert atmosphere, such as nitrogen or argon, is packaged with an oxygen scavenger and/or a desiccant, or is packaged under vacuum. The sealed packaging thus also serves to maintain the drug under the inert atmosphere. The degradation of the trientine in the pharmaceutical dosage forms of the invention is substantially prevented even at ambient (i.e. room) temperatures (20-25° C.).

DETAILED DESCRIPTION

Drugs may undergo decomposition, for example by oxidation, Such decomposition can be influenced by exposure to light and to reactive components of air, including oxygen, water and/or carbon dioxide. The stability of a pharmaceutical dosage form is related to maintaining its chemical, pharmaceutical and toxicological properties when stored, i.e., in a particular container and environment.

Trientine undergoes degradation, particularly when exposed to air and light. The pharmaceutical dosage form of the present invention comprises (i) trientine or a pharmaceutically acceptable salt of trientine, with or without compatible excipients, in a (ii) sealed packaging. The sealed packaging provides a convenient, accurate dosage form, while at the same time controls the local environment and prevents exposure of the drug to conditions that facilitates its decomposition.

Trientine as it is used herein refers to the free base form of the compound and also to the pharmaceutically acceptable salts of trientine. The term "pharmaceutically-acceptable salts" in this context, refers to the relatively non-toxic, inorganic and organic acid addition salts. Representative salts include the hydrochloride, hydrobromide, sulfate, bisulfate, phosphate, nitrate, acetate, stearate, laurate, benzoate, lactate, phosphate, tosylate, citrate, maleate, fumarate, succinate, tartrate, napthylate, and mesylate salts and the like. (See, for example, Berge et al. "Pharmaceutical Salts," J. Pharm. Sci. (1977) 66:1-19). In particularly preferred embodiments, the trientine is present as a hydrochloride salt, and most preferably as the dihydrochloride salt.

It would be understood by a person of ordinary skill in the art that other amine-based drugs, and particularly amine-based chelators, may be used in the pharmaceutical formulations and methods of the present invention.

The sealed packaging according to the present invention refers to any packaging that provides a high barrier protection against air, moisture and light. The term sealed packaging includes pouches, sachets, blister packs, and the like.

The sealed packaging may be formed from one or more materials comprising aluminum, aluminum foil laminates, polymers (PETs, polyethylene, polypropylene, etc.), polymer film laminates, paper laminates, etc. The sealed packaging preferably is made to comprise a material which renders the product opaque to light. Additionally, the material(s) for the sealed packaging are selected to have good barrier properties to exclude oxygen, water, etc.

In certain preferred embodiments of the invention, the sealed packaging contains a single-use quantity of the trientine. For example, a sachet may contain an amount of trientine hydrochloride crystals that provides a single therapeutic dose of trientine. Alternatively, each compartment of a blister pack may contain a single capsule or tablet that provides a single therapeutic dose of trientine. Accordingly, the exposure of a single dosage of trientine to atmospheric conditions upon dispensing for patient ingestion does not expose other unit dosages of the trientine to conditions that may facilitate its decomposition.

The pharmaceutical formulation may comprise a particulate composition of the drug, such as granules comprising the trientine, or loose crystals of the drug, with an appropriate set of excipients, which are disposed within the sealed packaging, for example a sachet. Alternatively, the pharmaceutical formulation may comprise a tablet or a capsule, which is disposed within the sealed packaging, for example a blister pack. Depending on the formulation of the drug (i.e., tablet, capsule, sachet, etc.), the formulation may be swallowed whole (tablet, capsule), or the formulation may be added to a vehicle such as drinking water for consumption.

In preferred embodiments, the trientine is packaged under conditions that exclude oxygen and moisture. Accordingly, in preferred embodiments the trientine is packaged within the sealed packaging in an inert atmosphere, such as nitrogen or argon. Packaging under nitrogen is preferred. Other embodiments could include packaging the trientine in a sealed unit package under vacuum or together with an oxygen scavenging agent and/or a desiccant to lower oxygen and/or water levels within the package. Also the packaging is preferably done under conditions of very low moisture. The sealed packaging thus also serves to maintain the drug under the inert atmosphere.

What is claimed is:

1. A solid oral dosage form comprising (i) trientine or a pharmaceutically acceptable salt of trientine, in a (ii) sealed packaging wherein the sealed packaging contains a single-use quantity of the trientine as a capsule or tablet packaged in an inert atmosphere.

2. The solid oral dosage form of claim 1 where the inert atmosphere is nitrogen.

3. The solid oral dosage form of claim 1 where degradation of the trientine is substantially prevented at ambient (i.e. room) temperatures (20-25° C.).

4. The solid oral dosage form of claim 3 where trientine is in the free base form.

5. The solid oral dosage form of claim 3 where trientine is in the form of the hydrochloride, dihydrochloride, hydrobromide, sulfate, bisulfate, phosphate, nitrate, acetate, stearate, laurate, benzoate, lactate, phosphate, tosylate, citrate, maleate, fumarate, succinate, tartrate, napthylate, or mesylate salt of trientine.

6. The solid oral dosage form of claim 3 where trientine is in the form of the hydrochloride or dihydrochloride salt of trientine.

7. The solid oral dosage form of claim 3 further comprising an amine-based chelator that is not trientine or a pharmaceutically acceptable salt of trientine, an oxygen scavenger, or a desiccant.

8. The solid oral dosage form of claim 3 wherein the dosage form is provided in a blister pack.

9. The solid oral dosage form of claim 3 where the sealed packaging is formed from one or more materials comprising aluminum, aluminum foil laminates, polymers, polymer film laminates, or paper laminates.

10. The solid oral dosage form of claim 3 where the sealed packaging is formed from a polymer selected from the group consisting of PETs, polyethylene, and polypropylene.

11. The solid oral dosage form of claim 3 where the sealed packaging contains a single therapeutic dose of trientine.

12. The solid oral dosage form of claim 1 where the trientine is present in a tablet or capsule disposed within a blister pack.

13. The solid oral dosage form of claim 1 comprising 250 mg of trientine.

14. A method of making the solid oral dosage form of claim 1 comprising packaging trientine under an inert atmosphere that excludes oxygen and moisture.

15. The method of claim 14 where the inert atmosphere is nitrogen.

16. A method of treating a disease or condition where excess copper is not removed from the body by administering to a patient in need thereof the solid oral dosage form of claim 3.

17. The method of claim 16 where the patient is a human.

18. The method of claim 17 where the disease or condition is Wilson's disease.

19. The method of claim 18 where the solid oral dosage form comprises 250 mg of trientine.

* * * * *